US008029843B2

(12) United States Patent
Bohm et al.

(10) Patent No.: US 8,029,843 B2
(45) Date of Patent: Oct. 4, 2011

(54) METHOD FOR THE EXTRACTION OF ALEURONE FROM BRAN

(75) Inventors: Arturo Bohm, Oberuzwil (CH); Carlo Bogoni, Winterthur (CH); Raimund Behrens, Constance (DE); Thomas Otto, Constance (DE)

(73) Assignee: Buhler AG, Uzwil (CH)

( * ) Notice: Subject to any disclaimer, the term of this patent is extended or adjusted under 35 U.S.C. 154(b) by 1637 days.

(21) Appl. No.: 10/344,809

(22) PCT Filed: Aug. 20, 2001

(86) PCT No.: PCT/CH01/00506
§ 371 (c)(1),
(2), (4) Date: Feb. 14, 2003

(87) PCT Pub. No.: WO02/15711
PCT Pub. Date: Feb. 28, 2002

(65) Prior Publication Data
US 2003/0175384 A1    Sep. 18, 2003

(30) Foreign Application Priority Data

Aug. 21, 2000 (DE) ................................. 10 41 156
Aug. 28, 2000 (DE) ................................. 100 42 488

(51) Int. Cl.
*A23L 1/10* (2006.01)
(52) U.S. Cl. ........................... 426/459; 426/463
(58) Field of Classification Search ............. 426/443, 426/455, 459, 460, 463, 464, 478, 481–483, 426/518
See application file for complete search history.

(56) References Cited

U.S. PATENT DOCUMENTS

| 2,400,459 | A | * | 5/1946 | Hall .............................. 159/4.09 |
| 2,930,699 | A | * | 3/1960 | De Sollano et al. ........... 426/331 |
| 3,449,130 | A | * | 6/1969 | Blanchon ........................ 426/31 |
| 4,560,471 | A |   | 12/1985 | Yamada et al. |
| 4,746,073 | A | * | 5/1988 | Stone et al. ........................ 241/9 |
| 4,919,952 | A | * | 4/1990 | Sadaranganey et al. ...... 426/254 |
| 5,082,680 | A | * | 1/1992 | Tkac .............................. 426/483 |
| 5,112,964 | A | * | 5/1992 | Aoe et al. ........................ 536/56 |
| 5,846,591 | A | * | 12/1998 | Satake et al. .................. 426/483 |
| 5,874,274 | A | * | 2/1999 | Jakobsen et al. .............. 435/200 |
| 6,147,206 | A | * | 11/2000 | Doner et al. .................. 536/128 |
| 6,231,866 | B1 | * | 5/2001 | Mann ............................ 424/732 |
| 6,255,505 | B1 | * | 7/2001 | Bijl et al. ...................... 554/227 |
| 2002/0037331 | A1 | * | 3/2002 | Hwang et al. ................. 424/750 |

FOREIGN PATENT DOCUMENTS

| DE | 3921023 C1 | | 8/1990 |
| EP | 0810031 A2 | * | 5/1997 |
| JP | 1206962 A | | 8/1989 |
| JP | 5219976 A | | 8/1993 |

OTHER PUBLICATIONS

Saunders et al, Enzymatic processing of Wheat Bran: Effect on nutrient availability, American Asoociation of Cereal Chemists, Jul. 1972, pp. 436-442.*
Kent, N.L.; Evers, A.D. (1994). Technology of Cereals (4th Edition). Woodhead Publishing. Online version available at: pp. 129-148 and 259-268. http://knovel.com/web/portal/browse/display?_EXT_KNOVEL_DISPLAY_bookid=304&VerticalID=0.*
Perry, R.H.; Green, D.W. (1997). Perry's Chemical Engineers' Handbook (7th Edition). (pp. 20-22 to 20-23). McGraw-Hill.*
Kent, N.L.; Evers, A.D. (1994). Technology of Cereals (4th Edition). Woodhead Publishing. pp. 129-148 and 259-268.*

* cited by examiner

*Primary Examiner* — Jyoti Chawla
(74) *Attorney, Agent, or Firm* — Bachman & LaPointe, P.C.

(57) ABSTRACT

The invention relates to a method for the preparation of aleurone from bran, in particular, wheat bran, for the extraction of aleuronic cells in particular from wheat grain, whereby the mainly aleurone-containing aleuronic components are separated from the mainly non-aleurone-containing non-aleuronic components in the bran and the aleurone-containing components are then isolated. The separation can be achieved by biochemical/enzymatic means and/or by mechanical-abrasive means. The subsequent isolation and extraction can be achieved by wet and/or dry separating methods.

49 Claims, No Drawings

METHOD FOR THE EXTRACTION OF ALEURONE FROM BRAN

The invention relates to a method for processing bran, in particular wheat bran, and extracting aleurone cells, in particular those of wheat kernels. Furthermore, it relates to the use of the separated or isolated aleurone components as an additive to foodstuffs and feedstock, or as a food supplement or feed supplement. In addition, it relates to aleurone-containing products and in particular to aleurone-containing functional food.

A wheat kernel can be divided into three primary components, namely the hull (or "bran"), endosperm, and germ. The hull itself consists of several finely differentiated layers, which may also be classified in three groups:

Pericarp (epidermis, longitudinal cells, cross cells, tube cells)

Seed coat or testa (pigmented layer, colorless layer)

Aleurone layer

The aleurone cell layer of wheat is a single-row layer consisting of thick-walled cells, the contents of which are very important from a nutritional and physiological perspective. The aleurone cells contain vitamins, minerals, fats, protein, phosphorous, and fibers (cell wall), among other things. The aleurone layer is the outermost boundary layer of the endosperm, and it is thus botanically part of the endosperm and not the hull. The cohesion between the aleurone cell layer, the very thin hyaline layer, and the seed coat due to very strong adhesive forces is particularly evident during mechanical separation of the endosperm and hull ("cleaning the bran"). Thus from a milling standpoint, the aleurone cell layer is part of the bran or hull, which may later be used as bran for eating or feedstock.

The endosperm of a cereal grain and in particular of a kernel of wheat is surrounded by multi-layered hulls. The pericarp is located on the exterior, consisting of the epidermis, cross cells, and tube cells. Moving inward toward the endosperm, next comes the seed coat, followed by the nutritionally and physiologically important aleurone cells after a hyaline layer. These aleurone cells contain many minerals, vitamins, and fibers, and they are adulterated with very few contaminants because they are protected by the pericarp and seed coat.

Although the pericarp can be separated from the seed coat relatively easily, it is very complicated to separate the aleurone cells from the seed coat. Therefore, the entire batch of bran is usually allocated for use as feedstock or bran for eating. Hydrothermal stabilization is performed according to DE-A-4435453 in order to obtain storable bran for this purpose.

It is also a well-known method to produce oxidation-resistant rice bran according to Japanese publication number 11103803 by extracting the bran from steeping water after the rice is processed ("rice polishing"). For this purpose, an agent is first added to the steeping water, and the water is subsequently removed by thermal treatment. This forms relatively large bran particles at the same time. Bran is also obtained whole with this method.

U.S. Pat. No. 5,082,680 describes a costly mechanical method for the layer-by-layer separation of bran. With this method, the bran is removed layer-by-layer by using four polishing or scouring steps and a scrubbing stage with two wettings. After the first wetting of the cleaned, dry wheat, it is allowed to stand. The epidermis is then removed from the pericarp during the first polishing stage.

After the second wetting, cross cells and tube cells are removed from the pericarp during the second polishing stage. These bran layers are sifted to separate the germs from the ground grain. Due to their assumed low levels of phytate phosphorous content, these sifted bran layers should be used as a food additive.

In the third polishing stage, the seed coat, portions of the hyaline layer, and aleurone cells are removed.

In addition to any remaining seed coat, the fourth polishing stage specifically removes the aleurone layer, which is no longer considered worth processing.

During final scrubbing, the bran residue which is still adhering and the germs are removed, followed by cooling and wetting; it is then allowed to stand.

This prior art certainly hints at a partial use of bran; however, it does not offer any solution for the specific removal and use of aleurone cells.

The underlying problem of the invention is to avoid the indicated disadvantages of the prior art and to extract the physiologically highly valuable aleurone components, in particular those of wheat kernels, from the bran containing them in the most complete and careful manner possible.

An additional problem is to make the aleurone components extracted in this manner specifically suited for addition to and to add them to human and animal food.

These problems are solved by separating the predominantly aleurone-containing aleurone components from the predominantly aleurone-free non-aleurone components and subsequently removing the aleurone-containing components. The removed aleurone components are then added to conventional foodstuffs as an additive or as a separate supplement.

The bran can be removed with biochemical enzymatic processes, mechanical abrasive processes, or by any combination of biochemical enzymatic and mechanical abrasive treatment.

During biochemical enzymatic treatment, the bran is kept in a container filled with water at an optimal temperature and an optimal pH value for enzymes. A biochemically active substance containing enzymes is added so that the adhesive forces between the aleurone cell layer and the brown seed coat are weakened by the enzymes in such a way that the aleurone tissues can easily be separated from the seed coat undamaged by means of a mild mechanical action.

It is expedient for the bran first to be reduced to a size of 400-800 μm, which will preferably free the bran of any endosperm still adhering to it.

The aleurone tissues will preferably be separated from the seed coat undamaged by means of a mild mechanical action. It is convenient if the mechanical action is applied to the bran in the form of active shearing forces. For example, this may be accomplished by directing the liquid in which the bran is being kept into a colloid mill, by which the shearing forces are then applied. The mechanical action may also be applied by means of an extruder.

In one particularly preferred embodiment, the cell walls of the aleurone cells are at least partially ruptured by the biochemical substance so that the contents of the aleurone cells can escape. More or less complete enzymatic degradation of the aleurone cell walls may be preferred for nutritional and physiological reasons, as required. These cell walls are hemicellulose, which is an important necessary element of life for certain intestinal bacteria.

Surprisingly, it has been shown that an aleurone layer and its individual cells can be separated from the firmly adhering seed coat by weakening their adhesion. This is preferably accomplished by means of suitable enzymes; for example, endoxylanase/arabinoxylanase. Rinsing in cold water promotes the weakening of the adhesive bond.

Aggregates of aleurone cells with intact cell walls or cells in solution are obtained, the contents of which can be separated and degraded.

The enzymes to be used are also quite safe for human food, so the aleurone cells or their contents (proteins, vitamins, etc.) in particular may be used for or in dietary foodstuffs.

It has been shown that the adhesive forces between the aleurone cells and the quite tenacious brown seed coat can be neutralized by the use of enzymes and mild mechanical impaction, thus resulting in the release of intact aleurone cells from the seed coat.

This is accomplished primarily by enzymes with xylanase action and mild mechanical impaction by means of a centrifugal mill.

In addition, it has been shown that the aleurone cells can be completely dissolved by treating bran with enzymes; thus, it is possible to separate the aleurone cell contents and their cell wall fragments from the hull components situated above them which remain undamaged, in particular those of the seed coat. This is primarily done with an enzyme mixture of xylanase, betaglucanase, cellulose, and arabinase.

SUMMARY

Either intact or degraded aleurone cells or their contents are obtained under the appropriate conditions.

The enzymes used are quite safe for human food.

An additional advantage is provided by the possibility of analytical access to individual layers.

It is expedient for predominantly aleurone-containing components and predominantly aleurone-free components of the bran located in the hydrated mixture to be separated or isolated from one another.

This separation or isolation can be accomplished with the "wet" version of the invented method, whereby the hydrated mixture of enzymatically treated bran is pressed, so that dissolved and suspended aleurone components are carried in the hydrated phase as aleurone juice, and the remaining bran components remain in the press as press cake. Alternatively, the hydrated mixture of enzymatically treated bran can be filtered, so that dissolved and/or suspended aleurone components are carried in the hydrated phase as aleurone juice, and the remaining bran components remain in the filter as filter residue.

However, the hydrated mixture of enzymatically treated bran can also be separated into the aleurone components and the non-aleurone components by decanting. Or they can be separated in two non-mixable liquids into the aleurone components and the non-aleurone components due to differences in wettability and/or differences in solubility. In some cases, it is also possible and quite convenient to perform the separation or isolation by a combination of the aforementioned separation steps. Both the same and different separation steps can be performed in sequence on the same hydrated mixture.

To separate or isolate the different aleurone components from one another, the aleurone juice in which the aleurone components are carried will preferably be centrifuged. The aleurone juice can also be filtered by microfiltration and/or ultrafiltration for this purpose. It can even be subjected to reverse osmosis in order to separate or isolate additional specific aleurone components. In this manner, different fractions of aleurone components can be extracted which can be specifically used in functional food.

Water will preferably be extracted from the aleurone juice in which the aleurone components are carried in order to increase the concentration of aleurone components, so that concentrated aleurone juice is extracted. Alternatively, an aleurone powder consisting of aleurone components can be produced by spray drying, freeze drying, or vacuum drying. Pre-concentration will preferably be carried out in an evaporator before producing the aleurone powder. In particular, dissolved proteins are precipitated in the aleurone juice by heating the aleurone juice or by salting out the proteins. The aleurone-containing products extracted in this way can be handled quite easily.

In order to obtain a product which does not alter its properties and which keeps well, the hydrated mixture or the aleurone juice, which contains the aleurone components and the biochemically active substance with the enzymes, is pasteurized after a sufficiently long period of enzymatic activity before concentration or pulverization.

In the "dry" version of the mechanical abrasive treatment of the bran, the aleurone components are separated from the non-aleurone components in a rolling mill, a centrifugal impact mill, or a jet mill. These methods can also be combined, if required. It is expedient for the bran to be moistened before it is subjected to mechanical abrasive treatment.

In one particularly convenient embodiment of the invented method, i.e. the "wet" version of the mechanical abrasive treatment, the bran is added to water and the aleurone components are separated from the non-aleurone components in a colloid mill or in a ball mill in which plastic balls of the same thickness as the bran will preferably be used.

The aleurone components and non-aleurone components separated from one another in the dry or the wet method are graded and sorted into fractions. The grading and sorting of the mixture of aleurone components and non-aleurone components can also be performed by air-classification, if necessary after prior drying. It is preferable to use a channel impeller air-classifier, a zigzag air-classifier, or a cross-flow air-classifier for this purpose. Combinations of these types of air-classifiers can also be used here, if required.

In another convenient embodiment, the fine particles of a fine fraction extracted by air-classification are removed before they are subjected to additional grading by sieving.

This prevents the sieves from becoming plugged by the buildup of fine particles on them. Grounded metallic sieves will preferably be used for sieving. This will reduce the risk of the fine particles becoming charged and an agglomeration of these fine particles forming. In any necessary additional steps for separation or isolation, such agglomerations of fine particles would produce adulterated fractions.

Following grading or sorting by air-classification, there is grading or sorting in an electrical field, if required. Both spatially homogenous and heterogeneous, temporally constant fields and alternating fields can be used. This allows different particles to be separated from one another due to their different electrical charges and/or their different electrical polarization.

For example, if a channel impeller air-classifier is used to process the wheat bran, whereby the different particles of the coarse fraction of the bran, which contains both non-aleurone hull particles originating in the furrow of the wheat kernel and aleurone particles, are electrically charged and/or polarized due to static electricity in various ways during their passage through the arched or in particular the circular channel of the channel impeller air-classifier because of the particles rubbing against one another and/or the channel wall and they follow a path through an area subjected to an electrical field after leaving the channel impeller air-classifier, this allows the collection of the non-aleurone hull particles originating in the furrow at one spot and the collection of the aleurone particles at a second spot different from the first spot. This separation is particularly convenient, because this makes the white to yellowish aleurone particles released from the dark hull particles of the furrow look cleaner visually. Furthermore, it should be mentioned that the furrow of wheat kernels can only be poorly cleaned, if at all, so it contains many unwanted substances and perhaps even environmental toxins.

In another embodiment, the mill product consisting of ground bran is separated by simultaneously directing the mill product into an inclined, vibrating channel at one spot, whose inclination, surface roughness, and vibration are designed in such a way that the different mill product components move along the channel at different migration speeds, which allows different mill product fractions with more or fewer aleurone components to be extracted at different spots further along the channel at successive time intervals.

However, it is preferable for the separation of the mill product consisting of the ground bran by means of the channel to be performed by simultaneously directing the mill product into an inclined, vibrating channel at one spot, whose inclination, surface roughness, and vibration are designed in such a way that the aleurone components migrate to the upper end of the channel while the non-aleurone components migrate to the lower end of the channel.

Another possibility for separating the mill product is sedimentation in a fluid-filled container, whereby different mill product fractions are extracted at the bottom of the container as sediment layers containing more or fewer aleurone components due to the differing sinking times of the various mill product components in the fluid-filled container.

The mill product can also be separated by moving the mill product particles along an equipotential surface of a heterogeneous electrical field, which causes the mill jet or the mill stream to be split into fractions containing more or fewer aleurone components due to the differing dielectric properties of the mill product particles. For example, the jet of mill product particles can be moved by means of a laminar-flow carrier fluid flowing through an equipotential surface of the electrical field in a defined path and thereby be split by the heterogeneous electrical field.

It is expedient for the mill product particles to become electrostatically charged by rubbing against one another and/or on part of the container and then moved transversely to an electrical field, which causes the mill jet or the mill stream to be split into fractions containing more or fewer aleurone components due to the differing electrical properties of the mill product particles. In particular, the jet of mill product particles is moved in a defined path by means of a laminar-flow carrier fluid flowing transversely to the electrical field and is then split by the electrical field.

Separation can also be accomplished by a combination of the aforementioned separation steps, whereby there is preferably only one switch from the "wet" method to the "dry" method.

After the fractionation of the bran components, e.g. by means of one of the aforementioned methods, the mill product fractions extracted can be further treated with a biochemical substance specific to each fraction. This allows the properties of the product to be specifically influenced. Therefore, it is quite reasonable first to isolate the different aleurone fractions from one another, then treat each fraction in a specific manner, and then to remix the specifically treated fractions. This makes it possible to alter the relative concentrations of the mixture prescribed by nature, which is important for the production of functional food.

The biochemical substance will preferably contain at least one of the enzymes betaglucanase, cellulose, xylanase, and arabinase in a hydrated medium with which the mill product fractions are mixed into a hydrated mixture.

It is particularly convenient if the biochemical substance contains at least one of the enzymes endoxylanase, beta-xylosidase, arabinofuranosidase, acetylesterase, xyloacetylesterase, and feruloyl esterase in this hydrated medium with which the mill product fractions are mixed.

It is preferable for the aleurone base of the food supplement or feed supplement to be in the form of a pressed pellet of aleurone components and a nutritionally and physiologically harmless binding agent. For example, the aleurone powder described above may be used in this production process.

The food supplement or feed supplement can also be in the form of a drink. The aforementioned concentrated aleurone juice, for example, may be used for this in a more or less concentrated form.

The additive or the food supplement or feed supplement can also be a powder. The aleurone powder described above may also be used for this purpose.

In addition, the foodstuff can be a starchy product or a dairy product. In principle, however, the aleurone-containing additive can be added to any desired processed food as a powder or as juice in order to produce functional food with a special physiological effect, special taste, special texture, etc.

Thus, a form of aleurone components isolated by specific microfiltration and/or specific centrifugation from the protoplasm of aleurone cells, for example, can be added to the functional food. A portion or all of the above-mentioned separated or isolated aleurone components may also be contained in the aleurone-containing product.

The invented functional food contains at least one of the substances contained in the aleurone extracted according to the methods described above.

The invented functional food may optionally contain aleurone cells which have been fully hydrolyzed by enzymatic action or aleurone cells which are still completely intact. The cell walls and cell contents of the "quasi-predigested" fully hydrolyzed aleurone cells can thus be applied directly to human metabolism. At the same time, the enzymatically partially hydrolyzed and thus "half predigested" aleurone cells with their "weakened" cell walls will be more easily digestible for humans on the one hand, but they will still be able to serve as food for intestinal bacteria on the other hand. Even the proportion of completely intact aleurone cells in this type of functional food will do a human being good, since the hemicellulose cell walls of the aleurone cells can be digested by human beings, at least with the cooperation of intestinal bacteria.

Additional benefits, features, and potential applications of the invention may be seen in the following description of some exemplary embodiments which are to be interpreted not to exclude other embodiments.

Wet Method:

Dry, cleaned wheat is stirred in a closed container filled with water mixed with enzymes.

The water is heated by the addition of the mechanical energy, or the tank may be equipped with a separate heating device to accelerate the heating process.

The pericarps are removed by the action of the enzymes and may be separated. After additional stirring, the seed coat also separates from the aleurone cells, which separate from the endosperm. The endosperms can now be removed and the aleurone cells in the water can be degraded separately.

EXAMPLE 1

Wheat bran with a size distribution of 400-8000µ is mixed with water and stirred at a temperature of 45-55° C., and an enzyme solution (xylanase, betaglucanase, cellulose, and arabinase) is added. Due to the action of individual or multiple enzymes, the aleurone cells can first be separated from the seed coat as tissue, and then be completely dissolved and thus sieved off of the remaining hull components. The aleurone cells are thereby dissolved, and the cell contents pour into the solution as protoplasm. The wet sieve residue contains the non-dissolved hull components (seed coats, pericarps). The wet sieved material contains the contents of the aleurone cells and their cell wall fragments.

This wet sieved material is concentrated into a yellowish-gray powder by spray drying and/or freeze drying.

EXAMPLE 2

Wheat bran with a size distribution of 400-800μ is mixed with water and stirred at a temperature of 45-55° C., and an enzyme solution (xylanase) is added. This causes weakening of the adhesive forces between the seed coat and the aleurone cell layer, resulting in the separation of the two layers adhering to one another. This effect can be optimized by mild mechanical action (centrifugal mill) without disrupting the tissues.

EXAMPLE 3

Wheat bran is mixed with water and stirred for an hour at a temperature of 45-50° C., and an enzyme solution (xylanase, betaglucanase, cellulose, and arabinase) is added. The remaining suspension is divided by a disperser for two minutes. The suspension which is left after this is sieved. The wet sieved material contains the degraded aleurone cells and their contents, while the sieve residue consists of seed coat which is completely free of aleurone cells.

Dry Method:

After cleaning in the bran centrifuge, the accumulated bran is dried and slightly heated. After being ground in a mill, where the actual separating action between the hull and aleurone layer should take effect, the mixture of bran components is sieved into fractions. It is then air-classified to sort the components of the hull (pericarp, testa) and aleurone with any adhering hull components. The separation, sieving, and sifting steps will naturally be repeated multiple times to obtain the desired level of enrichment of aleurone cells. The aleurone components obtained contain a concentration of at least 60% aleurone cells, and preferably more than 80%. Depending on their use, these components are further dried and ground, e.g. on a roller mill. The individual steps are described in greater detail below.

During the separation stage, the bran particles must be subjected to forces which cause the aleurone and hull to separate. If an impact mill is used, the pieces are substantially bent as a result of the forces applied (impact force, weight forces). With particle sizes of approximately >800 μm, this results in the pieces being fragmented and not separated. Only if the pieces fall below a certain size can the aleurone and hull definitely be separated by the action of the weight forces. The size of the particles at which separation occurs depends on the strength of the various layers (pericarp cellulose; testa hemicellulose; aleurone→hemicellulose) and the adhesive forces beneath the layers. Strength and adhesive force are significantly affected by moisture and temperature. For optimal separation conditions, the bran must first be thermally treated. Tests have shown that a product moisture between 8%-12%, preferably 10%, is optimal. In this case, the product temperature should not fall below 25 C. during separation.

Impact mill speeds of approximately 70 m/s (but <120 m/s) have proven to be beneficial. The sieve used should have a mesh size of 0.3-0.8 mm, preferably 0.5 mm. So-called "raffle" sieves (brand name Conidur) with 0.5 mm meshing produced good results.

In addition to impact forces, collision forces such as those occurring in a jet mill or a centrifugal impact mill have proven to be beneficial. The operations in a centrifugal impact mill (MIPS) are shown to have a beneficial effect on separation, because the flaky bran particles are lined up by the guide blade in the centrifuge rotor and the impact occurs on the edge. This allows weight forces to take effect without causing any bending stress to be applied to the particles and thus without fragmentation. This causes the hull and aleurone to be separated as larger pieces, and thus simpler devices can be used for sorting.

Thus, the method for extracting aleurone can be subdivided into 5 steps:
1. Drying/Heating
2. Separation
3. Sieving
4. Air-Classification (Sifting)
5. Fragmentation Experience shows that a bran particle goes through several cycles after drying. The number of cycles greatly depends on the desired quality (hull proportion). Particles which are part of the >500 μm fraction during sieving after the separation stage are directed back to the separation stage again, because the testa generally has not fully separated from the aleurone in this fraction. Depending on the desired quality, it must go through sieving and air-classification multiple times. Experience shows that particles >300 μm can be optimally sorted with a zigzag air-classifier. Particles <300 μm show a tendency to agglomerate, which suggests the channel impeller air-classifier. This type of sifter has the advantage of dispersing the agglomerations, and it also has a greater separating capacity.

As is well-known, fraction width and separating capacity play an important role in sorting. Tests have shown that favorable sieve fractions can be extracted for the subsequent air-classifiers by using the following mesh widths for sieving:
1. 400 μm
2. 300 μm
3. 200 μm
4. 150 μm
5. 100 μm Measurements of the most important minerals (Ca, Fe, K, Mg, P, Zn) have shown that the bran may be enriched by a factor of 2, and thus the proportion of hull components must be <10%. This is only inapplicable to the fraction which accumulates as sieved material (100 μm sieve). It is naturally quite difficult and thus costly to sort particles of this size (<100 μm).

If the intended use so requires, the aleurone cells may be broken up with a roller mill in a final step.

| Chemical Analysis of Aleurone Extracted with the Applicant's Method | | |
|---|---|---|
| Substance | Mass Content | Content per 100 g |
| Energy (estimated) | kcal/kJ | 2001/840 |
| Protein | g | 16 |
| Carbohydrates | g | 42 |
| Starch | g | 1 |
| Cellulose | g | 0 |
| of this, sugars | g | 12.9 |
| Free sugars | g | 8.6 |
| Raffinose | g | 2.6 |

-continued

Chemical Analysis of Aleurone Extracted with the Applicant's Method

| Substance<br>Energy (estimated) | Mass Content<br>kcal/kJ | Content per 100 g<br>2001/840 |
|---|---|---|
| of this, fat | g | 8 |
| Saturated fatty acids | g | 1.4 |
| Monounsaturated fatty acids | g | 1.4 |
| Polyunsaturated fatty acids | g | 5.2 |
| of this, edible fiber | g | 45 |
| Soluble | g | 15 |
| Insoluble | g | 30 |
| Vitamins | | |
| E (tocopherol) | mg | 6 |
| B1 (thiamin, aneurin) | mg | 1.3 |
| B2 (riboflavin, lactoflavin) | mg | 1 |
| B6 (pyridoxine, adermine) | mg | 4 |
| Folic acid | g | 300 |
| Niacin, nicotine amide | mg | 35 |
| Pantothen acid | mg | 4.5 |
| Minerals (Ash) | | |
| Calcium (Ca) | mg | 2,225 |
| Magnesium (Mg) | mg | 915 |
| Phosphorous (P) | mg | 2,520 |
| Iron (Fe) | mg | 22 |
| Zinc (Zn) | mg | 28 |
| Phytochemicals | | |
| Phytic acid | g | 4.12 |
| Ferulic acid | mg | 5 |
| Caffeic acid | mg | 1 |
| Chlorogenic acid | mg | 1 |
| Lignans | g | 13 |
| Arabinoxylan | g | 29 |

The table shows the results of a chemical analysis of aleurone extracted with the invented method performed by the applicant.

The notable improvement of many body functions due to aleurone enrichment in food should be particularly emphasized. For example, polyunsaturated fatty acids have a positive effect on the heart/circulatory system and on cholesterol levels. Vitamin E (tocopherol) has a positive effect on the heart/circulatory system and cholesterol levels, as well as the colon. Vitamin B6 (pyridoxine, adermine) has a particularly positive effect on general health and well-being. Like magnesium, folic acid has an extremely positive effect on mental and physical performance. Iron also contributes to one's condition of general health and well-being. Both soluble and insoluble edible fibers have a very positive effect on digestion, the heart/circulatory system, and the colon.

The invention claimed is:

1. Method for processing bran and extracting aleurone cells, wherein the aleurone-containing aleurone components are separated from the aleurone-free non-aleurone components in the bran, and the aleurone-containing components are then removed, and wherein the aleurone-containing aleurone components are separated from the aleurone-free non-aleurone components by a mechanical force selected from the group consisting of impact forces, collision forces and combinations thereof, and wherein a fraction comprising the aleurone components and non-aleurone components separated from one another and having particle sizes above 100 μm are graded and sorted into fractions by channel impeller air-classification.

2. Method according to claim 1, wherein the bran is first fragmented to a bran fragment size of about 400-800 μm.

3. Method according to claim 1, wherein the bran is first freed of endosperm.

4. Method according to claim 1, wherein grading or sorting is performed by a combination of channel impeller air-classification and at least one of zigzag air-classification and cross-flow air classification.

5. Method according to claim 1, wherein there is grading or sorting in an electrical field following grading or sorting by air-classification.

6. Method according to claim 1, wherein the bran is wheat bran and the aleurone cells are those of wheat kernels.

7. Method according to claim 1, wherein separation is carried out in an impact mill operating at a speed in the range of approximately 70 m/s to <120 m/s.

8. Method according to claim 1, wherein separation is carried out such that no bending stress is applied to the bran while weight forces take effect on the bran.

9. The method according to claim 1, wherein the fraction comprising the aleurone components and non-aleurone components which is sorted into fractions by channel impeller air-classification has particle sizes above 100 μm and less than 300 μm.

10. Method according to claim 1, wherein the fine particles of a fine fraction extracted by air-classification are removed before they are subjected to additional grading by sieving.

11. Method according to claim 10, wherein grounded metallic sieves are used for sieving.

12. Method according to claim 1, wherein moisture and temperature during separation are controlled so as to allow optimal separation conditions.

13. Method according to claim 12, wherein the moisture is controlled in a range of between 8%-12% during separation, and wherein the temperature is controlled to not fall below 25° C. during separation.

14. Application of the aleurone components separated or isolated by the method according to claim 1 as an additive in foodstuffs or feedstock, or as a food supplement or feed supplement.

15. Application according to claim 14, wherein the food supplement or the feed supplement is a pressed pellet of aleurone components and a nutritionally and physiologically harmless binding agent.

16. Application according to claim 14, wherein the additive or the food supplement or feed supplement is a drink.

17. Application according to claim 14, wherein the additive or the food supplement or feed supplement is a powder.

18. Application according to claim 14, wherein the food supplement is a starchy product.

19. Application according to claim 14, wherein the food supplement is a dairy product.

20. Aleurone-containing product containing the aleurone components separated or isolated according to claim 1.

21. Product according to claim 20, wherein the product is a powdered aleurone concentrate.

22. Product according to claim 20, wherein the product is an aleurone juice concentrate.

23. Method according to claim 1, wherein the aleurone tissues are separated from the seed coat undamaged by means of a mild mechanical action.

24. Method according to claim 23, wherein the mechanical action is applied to the bran in the form of active shearing forces.

25. Method according to claim 24, wherein the mechanical action is applied to the bran by means of an extruder.

26. Method according to claim 1, wherein separation is performed by mechanical and abrasive action.

27. Method according to claim 26, wherein separation of the aleurone components from the non-aleurone components is performed in a roller mill.

28. Method according to claim 26, wherein separation of the aleurone components from the non-aleurone components is performed in a centrifugal impact mill.

29. Method according to claim 26, wherein separation of the aleurone components from the non-aleurone components is performed in a jet mill.

30. Method according to claim 26, wherein separation of the aleurone components from the non-aleurone components is performed by a combination of the separation steps in claims 27 through 29.

31. Method according to claim 26, wherein the bran is moistened before it is subjected to the mechanical abrasive treatment.

32. Method according to claim 26, wherein the bran is added to water and the aleurone components are separated from the non-aleurone components in a colloid mill.

33. Method according to claim 26, wherein the bran is added to water and the aleurone components are separated from the non-aleurone components in a ball mill.

34. Method according to claim 33, wherein plastic balls are used in the ball mill.

35. Method according to claim 1, wherein the process is used to process wheat bran and whereby the different particles of the coarse fraction of the bran, which contains both non-aleurone hull particles originating in the furrow of the wheat kernel and aleurone particles, are electrically charged and/or polarized due to static electricity in various ways during their passage through the arched channel of the channel impeller air-classifier because of the particles rubbing against one another and/or the channel wall and they follow a path through an area subjected to an electrical field after leaving the channel impeller air-classifier, allowing the collection of the non-aleurone hull particles originating in the furrow at one spot and the collection of the aleurone particles at a second spot different from the first spot.

36. Method according to claim 35, wherein the arched channel is a circular channel.

37. Method according to claim 35, wherein the mill product consisting of ground bran is separated by simultaneously directing the mill product into an inclined, vibrating channel at one spot, whose inclination, surface roughness, and vibration are designed in such a way that the different mill product components move along the channel at different migration speeds, which allows different mill product fractions with more or fewer aleurone components to be extracted at different spots further along the channel at successive time intervals.

38. Method according to claim 37, wherein the separation of the mill product consisting of the ground bran by means of the channel is performed by simultaneously directing the mill product into an inclined, vibrating channel at one spot, whose inclination, surface roughness, and vibration are designed in such a way that the aleurone components migrate to the upper end of the channel while the non-aleurone components migrate to the lower.

39. Method according to claim 37, wherein the mill product is separated by sedimentation in a fluid-filled container, whereby different mill product fractions are extracted at the bottom of the container as sediment layers containing more or fewer aleurone components due to the differing sinking times of the various mill product components in the fluid-filled container.

40. Method according to claim 37, wherein the mill product is separated by moving the mill product particles along an equipotential surface of a heterogeneous electrical field, which causes the mill jet or the mill stream to be split into fractions containing more or fewer aleurone components due to the differing dielectric properties of the mill product particles.

41. Method according to claim 40, wherein the jet of mill product particles is moved by means of a laminar-flow carrier fluid flowing through an equipotential surface of the electrical field in a defined path and is thereby split by the heterogeneous electrical field.

42. Method according to claim 37, wherein the mill product particles become electrostatically charged by rubbing against one another and/or on part of the container and are then moved transversely to an electrical field, which causes the mill jet or the mill stream to be split into fractions containing more or fewer aleurone components due to the differing electrical properties of the mill product particles.

43. Method according to claim 42, wherein the jet of mill product particles is moved in a defined path by means of a laminar-flow carrier fluid flowing transversely to the electrical field and is then split by the electrical field.

44. Method according to claim 35, wherein separation is performed by a combination of the separation steps in claims 37 through 43.

45. Method according to claim 35, wherein the mill product fractions extracted are further treated with a biochemical substance specific to each fraction.

46. Method according to claim 45, wherein the biochemical substance contains at least one of the enzymes betaglucanase, cellulase, xylanase, and arabinase in a hydrated medium with which the mill product fractions are mixed into a hydrated mixture.

47. Method according to claim 45, wherein the biochemical substance contains at least one of the enzymes endoxylanase, beta-xylosidase, arabinofuranosidase, acetylesterase, xyloacetylesterase, and feruloyl esterase in a hydrated medium with which the mill product fractions are mixed into a hydrated mixture.

48. Method for processing bran and extracting aleurone cells, comprising the steps of:
separating aleurone-containing components from hull components in the bran by subjecting the bran to impact and/or collision forces in a mill;
sieving the bran including separate aleurone-containing components and hull components into fractions of different particle sizes including a fraction having a particle size of greater than 100 µm; and
air-classifying the fraction having particle sizes of greater than 100 µm by channel impeller air-classification to separate the aleurone-containing components from the hull components.

49. The method according to claim 48, wherein the air-classifying step is carried out on a fraction having particle sizes greater than 100 µm and less than 300 µm.

* * * * *